United States Patent
Fairfax et al.

(10) Patent No.: US 6,265,579 B1
(45) Date of Patent: Jul. 24, 2001

(54) PROCESS FOR PREPARING PIPERAZINE-SUBSTITUTED ALIPHATIC CARBOXYLATES

(75) Inventors: David John Fairfax, Delmar; Pedro E. Hemandez, Schoharie, both of NY (US); Erik T. Michalson, Charles City, IA (US)

(73) Assignee: Salsbury Chemicals, Inc., Charles City, IA (US)

( * ) Notice: Subject to any disclaimer, the term of this patent is extended or adjusted under 35 U.S.C. 154(b) by 0 days.

(21) Appl. No.: 09/429,660

(22) Filed: Oct. 29, 1999

(51) Int. Cl.$^7$ .................................................. C07D 295/15
(52) U.S. Cl. ................................................................ 544/396
(58) Field of Search ................................................. 544/396

(56) References Cited

U.S. PATENT DOCUMENTS

| | | | |
|---|---|---|---|
| 4,525,358 | * | 6/1985 | Baltes et al. ........................ 514/255 |
| 5,502,212 | * | 3/1996 | Bonrath et al. ....................... 548/236 |

FOREIGN PATENT DOCUMENTS

| | | | |
|---|---|---|---|
| 2225320 | * | 5/1990 | (GB) . |
| 163415 | * | 3/1994 | (PL) . |

OTHER PUBLICATIONS

Bobrowska et al., Chemical Abstracts, vol. 123, No. 55923s (Abstract for Pl 163,415, Mar. 31, 1994), 1995.*
Encyclopedia of Chemical Technology by Kirk–Othmer, vol. 5, pp. 374–383, 1993.*

* cited by examiner

Primary Examiner—Emily Bernhardt

(74) Attorney, Agent, or Firm—Richard J. Hammond

(57) ABSTRACT

A process is disclosed for the preparation of a piperazine-substituted aliphatic carboxylate having the formula

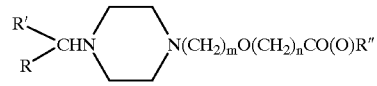

where m and n are individually an integer of from 1 to 6, R and R' are the same or different and are hydrogen, $C_1$ to $C_6$ alkyl or aryl or heteroaryl that is unsubstituted or is substituted with at least one substituent that is halo, $C_1$ to $C_6$ alkyl or $C_1$ to $C_6$ alkoxy and R" is $C_3$ to $C_{12}$ branched alkyl or an organic or inorganic cation. The process comprises treating a solution comprising a compound of the formula

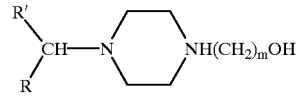

wherein m, R and R' are as defined above and an aliphatic ester of the formula

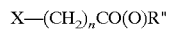

where X is a leaving group and n and R" are as defined above, with a base in the presence of an effective amount of a phase transfer catalyst, for a time and at a temperature sufficient to form a piperazine-substituted aliphatic carboxylate. Hydrolysis of the carboxylate with acid produces a piperazine-substituted aliphatic carboxylic acid or the acid salt thereof.

10 Claims, No Drawings

PROCESS FOR PREPARING PIPERAZINE-SUBSTITUTED ALIPHATIC CARBOXYLATES

FIELD OF INVENTION

This invention relates to an improved method for preparing aliphatic esters and carboxylic acids substituted with a piperazinyl alkoxide group. More particularly, this invention relates to the preparation of aliphatic carboxylic acids substituted with a 1-alkoxy4-alkylpiperazinyl group.

BACKGROUND OF THE INVENTION

U.S. Pat. No. 4,525,358 discloses the preparation of aliphatic carboxylic acids substituted with 1-alkoxy-4-alkylpiperazines having the formula

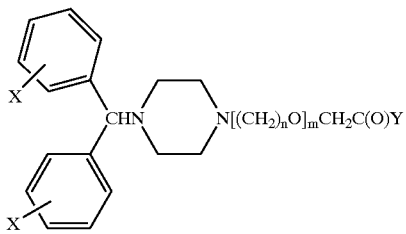

where Y is an ester, hydroxy or amino group, X and X' are independently hydrogen, halo, linear or branched lower alkoxy or trifluoromethyl and m and n are the integers 1 or 2. A number of reaction routes for the preparation of these acetic acid derivatives are shown, e.g., the reaction of 1-(diphenylmethyl)-piperazine with an omega haloacetamide followed by hydrolysis, the reaction of the alkali metal salt of an omega-[4-(diphenylmethyl)-1-piperazinyl]alkanol with a 2-haloacetamide followed by hydrolysis, etc.

UK Patent Application 2,225,321, published on May 30, 1990 discloses that 2-[2-[4-[(4-chlorophenyl)phenylmethyl]-1-piperazinyl]ethoxy]-acetic acid, i.e., the compound shown above where Y is hydroxy, X is hydrogen, X' is chloro and m and n are the integer 1, may be prepared by hydrolyzing 2-[2-[4-[(4-chlorophenyl)phenylmethyl]-1-piperazinyl]ethoxy]-acetonitrile with base or with acid. The nitrile is prepared by reaction of racemic 1-[(4-chlorophenyl)-phenylmethyl]-piperazine with 2-chloroethoxyacetonitrile.

UK Patent Application 2,225,320, published May 30, 1990 discloses the preparation of 2-[2-[-4-[(4-chlorophenyl)phenylmethyl]-1-piperazinyl]ethoxy]-acetic acid by the reaction of 2-[4-[(4-chlorophenyl)-phenylmethyl]-piperazinyl]1-ethan-1-ol with an alkali metal haloacetate in the presence of an alkali metal alcoholate followed by removal of the alkali metal salt with acid to form the free acid or its acid salt.

In a reaction that uses one of the same starting materials disclosed in the UK '320 application, Polish patent PL 163415 B1 published on Apr. 21, 1992 discloses the reaction of 2-[4-[(4-chlorophenyl)-phenylmethyl]-piperazinyl]1-ethan-1-ol with chloroacetic acid, in a two phase system that is an organic phase (the substrate and an inert solvent) and an inorganic phase (the hydroxide of an alkali metal in water). A yield of 67% of 2-[2-[4-[(4-chlorophenyl)-phenylmethyl]-1-piperazinyl]ethoxy]-acetic acid from this reaction was reported.

It would be desirable to have synthetic routes for the preparation of the physiologically active compounds similar to those of compound I that result in higher yields or higher purity products.

SUMMARY

A process is disclosed for the preparation of a piperazine-substituted aliphatic carboxylate having the formula

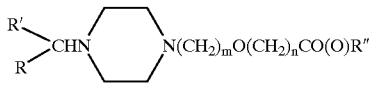

where m and n are individually an integer of from 1 to 6, R and R' are the same or different and are hydrogen, $C_1$ to $C_6$ alkyl or aryl or heteroaryl that is unsubstituted or is substituted with at least one substituent that is halo, $C_1$ to $C_6$ alkyl or $C_1$ to $C_6$ alkoxy and R" is $C_3$ to $C_{12}$ branched alkyl or an organic or inorganic cation. The process comprises treating a solution comprising a compound of the formula

wherein m, R and R' are as defined above and an aliphatic ester of the formula

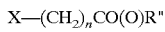

where X is a leaving group and n and R" are as defined above, with a base in the presence of an effective amount of a phase transfer catalyst, for a time and at a temperature sufficient to form a piperazine-substituted aliphatic carboxylate. Hydrolysis of the carboxylate with acid produces a piperazine-substituted aliphatic carboxylic acid or the acid salt thereof

DESCRIPTION OF THE PREFERRED EMBODIMENTS

In the process of the present invention to prepare a piperazine-substituted aliphatic carboxylate the following definitions apply:

The phrase "$C_1$ to $C_6$ alkyl" is intended to mean and include linear or branched alkyl groups having from one to six carbon atoms such as methyl, ethyl, n-propyl, isopropyl, n-butyl, secondary butyl, tertiary butyl, n-pentyl, 2-methylbutyl, n-hexyl and the like.

The phrase "$C_1$ to $C_6$ alkoxy" is intended to mean and include linear or branched alkoxy groups having from one to six carbon atoms such as methoxy, ethoxy, n-propoxy, isopropoxy, n-butoxy, secondary butoxy, tertiary butoxy, n-pentoxy, 2-methylbutoxy, n-hexlyoxy and the like.

The phrase "aryl or heteroaryl that is unsubstituted or substituted with at least one substituent that is halo, $C_1$ to $C_6$ alkyl or $C_1$ to $C_6$ alkoxy is intended to mean and include the unsubstituted aryl groups such as illustrated by phenyl, 1-naphthyl, 2-naphthyl and the like, the unsubstituted heteroaryl groups such as illustrated by furanyl, thiophenyl, pyrrolyl, pyranyl, pyridinyl and the like as well as the illustrated unsubstituted aryl or heteroaryl groups substituted by at least one halo such as chloro, bromo, etc., $C_1$ to $C_6$ alkyl or $C_1$ to $C_6$ alkoxy such as those shown above.

The phrase "$C_3$ to $C_{12}$ branched alkyl" is intended to mean and include branched alkyl groups having from three to twelve carbon atoms such as isopropyl, 2-methylpropyl, 2-methylbutyl, 2-methylpentyl, 3-methylhexyl, 3-methyloctyl and the like.

The phrase "X is a leaving group" is intended to mean and include leaving groups which are those organic moieties commonly the subject of unimolecular, multistage or bimolecular, concerted elimination reactions and include the moieties illustrated by halo (Cl, Br or I ), $OSO_2R$, OCOR, OR, $NR_3$, $PR_3$, $SR_2$, $SO_2R$, and the like, where R is defined above. Such leaving groups are well known in the prior art.

The word "base" is intended to mean and include an ammonium, alkali metal or alkaline earth metal hydroxide, carbonate or (if appropriate) bicarbonate, hydride or amide such as sodium hydroxide, potassium hydroxide, sodium carbonate, sodium bicarbonate, lithium hydride, sodamide and the like.

The term "phase-transfer catalyst" is intended to mean and include the group of compounds that effect reactions between two separate phases of a reaction mixture. In the preferred embodiment of the process of the present invention, such phase-transfer catalyst is of the "biphasic" type (it is a solid/liquid phase-transfer catalyst and not necessarily one that promotes organic/aqueous phase reactions). Phase transfer are well known in the prior art and include $C_3$ to $C_{12}$ branched alkyl (as defined above) ammonium halides, the $C_1$ to $C_6$ alkyl phosphonium halides, the unsubstituted or substituted aryl phosphonium halides and the like. See, for example, Kirk Othmer, 4$^{th}$ Ed., "PHASE-TRANSFER CATALYSTS, 5, pages 340–381 (1992).

The phrase "organic or inorganic cation" is intended to mean and include the cation employed to form the base as defined above and includes such cations as sodium, potassium, lithium, ammonium and the like.

The piperazine-substituted aliphatic carboxylate prepared in accordance with the process of the present invention comprises one or more compounds having the following formula

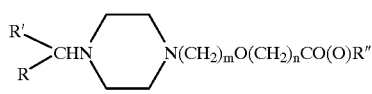

wherein m and n are individually an integer from 1 to 6, R and R' are the same or different and are $C_1$ to $C_6$ alkyl or aryl or heteroaryl that is unsubstituted or is substituted with at least one substituent that is halo, $C_1$ to $C_6$ alkyl or $C_1$ to $C_6$ alkoxy and R" is $C_3$ to $C_{12}$ branched alkyl or an organic or inorganic cation.

In the above piperazine-substituted aliphatic carboxylate compounds it is preferred that m and n are integers that are 1 or 2, R and R' are different and are aryl either unsubstituted or substituted with at least one substituent that is methyl, ethyl or chloro and R" is isopropyl, secondary butyl, tertiary butyl or neopentyl. Most preferably, m is 2, n is 1, R is hydrogen, R' is chloro and R" is tertiary butyl.

The process of the present invention requires that a solution is formed comprising a piperazine compound of the formula

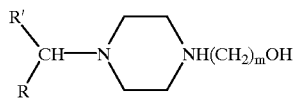

where n, R and R' are defined above and an ester of the formula

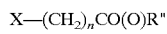

where X is a leaving group and n and R" are as defined above.

Preferably, the leaving group in the above ester is halo or an alkyl or aryl sulfonate, most preferably bromo, chloro or toluene sulfonate.

The solvent forming such solution may be any inert solvent (it does not react with the components of the solution) such as one that is aromatic, e.g., toluene, xylene, etc., a ketone, eg. acetone, 2-butanone, etc.

The solution of piperazine compound and ester are admixed with a base in the presence of an effective amount of a phase transfer catalyst, for a time and at a temperature sufficient to form a piperazine-substituted aliphatic carboxylate.

The base necessary to effect the reaction of the piperazine compound and the ester are preferably alkali metal or alkaline earth metal hydroxides such as sodium hydroxide or sodium carbonate. These bases are typically used as solids or they may be used as concentrated aqueous solutions, e.g. 15N.

As noted above, the phase-transfer catalyst is one that is effective in a biphasic system (solid\liquid phases) and includes such catalysts as a branched alkyl ammonium halide, alkyl phosphonium halide, aryl phosphonium halide, etc. Examples of such catalysts useful in carrying out the process of the present invention are tributyhexadecylphosphonium bromide, tetrabutylammonium hydrogen sulfate, benzyltriethylammonium chloride, tetrabutylammonium bromide, etc. These catalysts may be used in concentrations of from about 0.05% to about 15.0% based on the piperazine compound.

Typically, the temperature of the reaction needed to effect the condensation of the piperazine compound with the ester is room about –10° to about 40° C. for about one to about 24 hours. Most preferably, the reaction is started at 0° and after about 12 hours has reached a temperature of about 25° C.

Molar equivalents of ester and piperazine compound are used in the process of the present invention although a slight excess of ester (1.2 to 1.5 equivalents) are sometimes necessary to maximize yields.

The reaction of the present invention produces an aliphatic carboxylate, i.e., the compound produced is where R" is $C_3$ to $C_{12}$ branched alkyl. While physiologically active themselves, the compounds produced by the process of this invention are also useful as intermediates for the preparation of other physiologically active materials.

It should be noted that the branched substituent R" causes desirable effects in the production of the subsequent, physiologically active compounds. Thus, higher purity products are produced from the compounds arising from the process of the present invention. Enhanced yields of such products have been produced. $C_1$ to $C_6$ linear or branched alkyl As a further embodiment of the present invention, the purity of the compounds of the present invention, i.e. compound II have been enhanced by admixture of the reaction mixture produced from the treatment of the solution of the piperazine compound and the ester by base with an liquid, impurity separating agent. The unreacted starting materials as well as the undesirable by-products of the reaction are removed into(extracted by) the liquid, impurity separating agent. As a result, highly pure compound II is readily separated from the admixture. Liquid, impurity separating agents include compounds of the formula T—O—T' where T and T' are different and are $C_1$ to $C_6$ linear or branched alkyl. Preferably, one of the T or T' groups is branched. A particularly preferred liquid, impurity separating agent is methyl tertiary butyl ether.

The aliphatic carboxylates produced in the process of the present invention may be converted into a compound where R" is —OH (Cetirizine), by base hydrolysis. Typically, compound II is hydrolyzed by base to yield compounds where R" is an organic or inorganic cation depending on the base employed for hydrolysis. Further hydrolysis with acid produces the desired free carboxylic acid. Of course, acid hydrolysis may be used in place of base thereby forming the free carboxylic acid or the acid salt of this acetic acid derivative. These hydrolysis reactions are well known in the prior art.

The following example are submitted for the purposes of illustration only. They are not intended and should not be regarded as limiting the invention as defined herein in any way.

EXAMPLES

Example 1

A solution of 33.0 g (0.1 mole) of 1-[(4-chlorophenyl) phenylmethyl]-4-(2-hydroxyethyl)piperazine as the free base, 2.0 g of tetrabutylammonium bromide (the phase transfer catalyst) and 25.0 g (0.13 mole) of tert-butyl ammonium acetate in 200 mL of toluene and 200 mL of 15N sodium hydroxide solution is stirred at ambient temperature, i.e., 22° C., over a period of 18 hours. The reaction mixture is transferred to a separatory funnel where three layers separate after standing: a top, toluene-rich layer, a middle thick, white oily layer and a bottom, aqueous layer. The aqueous layer is discarded. The remaining two layers are combined and the solvents are removed by distillation under reduced pressure. The thick, white oily residue is dissolved in 200 mL of concentrated ammonium hydroxide, washed with methyl tert-butyl ether, acidified to a pH of about 4 with concentrated hydrochloric acid and extracted twice with 100 mL aliquots of 2-butanone. The organic phases are separated and the solvent removed from the combined extracts under reduced pressure. The resulting thick amber oily residue is dissolved in 100 mL of acetone. To this solution is added 18 mL of concentrated hydrochloric acid, then the resulting solution is filtered, diluted with 400 mL of acetone and stirred at ambient conditions for 18 hours. A white precipitate is produced which is vacuum filtered. The filter cake is washed with 100 mL of acetone, air dried for 30 minutes and vacuum dried at 40° C. for 6 hours. The resulting white powder is (RS2-[2-[4-[(4-chlorophenyl)phenyl methyl] piperazin-1-yl]ethoxy]acetic acid dihydrochloride, 35 g (76% yield).

Example 2

The procedure of Example 1 is repeated except that the amount of 15N sodium hydroxide solution used in the reaction solution is reduced by half, i.e., 100 mL of sodium hydroxide is used. This procedure produced 31.0 g of the (RS2-[2-[4-[(4-chlorophenyl)phenyl methyl]piperazin-1-yl] ethoxy]acetic acid dihydrochloride as a white powder (67% yield).

Example 3

The procedure of Example 1 is repeated except that the amount of 15N sodium hydroxide solution used in the reaction solution is reduced to 50 mL. This procedure produced 33.0 g of the (RS)-2-[2-[4-[(4-chlorophenyl) phenyl methyl]piperazin-1-yl]ethoxy]acetic acid dihydrochloride as a white powder (71% yield).

Example 4

The procedure of Example 1 is repeated except that tetrabutylammonium bromide is omitted. This procedure did not produce any (RS)-2-[2-[4-[(4-chlorophenyl)phenyl methyl]piperazin-1-yl]ethoxy]acetic acid dihydrochloride.

Example 5

The procedure of Example 1 is repeated except that 2.0 g of ALIQUATO® 336 Phase Transfer Catalyst is used in the reaction solution instead of tetrabutylammonium bromide. This procedure produced the (RS)-2-[2-[4-[(4-chlorophenyl)phenyl methyl]piperazin-1-yl]ethoxy]acetic acid dihydrochloride as a white powder in 82% yield (via chromatographic assay).

Example 6

The procedure of Example 1 is repeated except that 2.0 g of ADOGEN® 464 Phase Transfer Catalyst is used in the reaction solution instead of tetrabutylammonium bromide. This procedure produced the (RS)-2-[2-[4-[(4-chlorophenyl)phenyl methyl]piperazin-1-yl]ethoxy]acetic acid dihydrochloride as a white powder in 86% yield (via chromatographic assay).

Example 7

The procedure of Example 1 is repeated except that 2.0 g of TDA-1 is used in the reaction solution instead of tetrabutylammonium bromide. This procedure produced the (RS)-2-[2-[4-[(4-chlorophenyl)phenyl methyl]piperazin-1-yl] ethoxy]acetic acid dihydrochloride as a white powder in 99% yield (via chromatographic assay).

Example 8

The procedure of Example 1 is repeated except that 2.0 g of tetrabutylammonium hydrogen sulfate is used in the reaction solution instead of tetrabutylammonium bromide. This procedure produced the (RS)-2-[2-[4-[(4-chlorophenyl)phenyl methyl]piperazin-1-yl]ethoxy]-acetic acid dihydrochloride as a white powder in 91% yield (via chromatographic assay).

Example 9

The procedure of Example 1 is repeated except that 2.0 g of benzyltriethyl-ammonium chloride is used in the reaction solution instead of tetrabutylammonium bromide. This procedure produced the (RS)-2-[2-[4-[(4-chlorophenyl)phenyl methyl]piperazin-1-yl]ethoxy]acetic acid dihydrochloride as a white powder in 97% yield (via chromatographic assay).

Example 10

The procedure of Example 1 is repeated except that 2.0 g of cetyltrimethylammonium bromide is used in the reaction solution instead of tetrabutyl-ammonium bromide. This procedure produced the (RS)-2-[2-[4-[(4-chlorophenyl)phenyl methyl]piperazin-1-yl]ethoxy]acetic acid dihydrochloride as a white powder in 94% yield (via chromatographic assay).

Example 11

The procedure of Example 1 is repeated except that 2.0 g of tetrabutylphosphonium bromide is used in the reaction solution instead of tetrabutylammonium bromide. This procedure produced the (RS)-2-[2-[4-[(4-chlorophenyl)phenyl methyl]piperazin-1-yl]ethoxy]acetic acid dihydrochloride as a white powder in 76% yield (via chromatographic assay).

We claim:

1. A process for preparing a piperazine-substituted aliphatic carboxylic acid having the formula

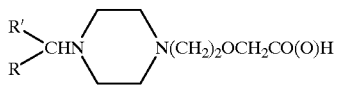

wherein R is phenyl and R' is 4-cholorophenyl, said process comprising (a) treating a solution comprising a compound of the formula

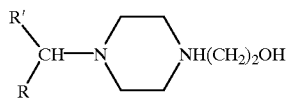

wherein R and R' are as defined above and an aliphatic ester of the formula

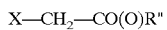

wherein X is a leaving group and R" is tert-butyl, with a base in the presence of an effective amount of a phase-transfer catalyst, for a time and at a temperature sufficient to form said piperazine-substituted aliphatic carboxylate of the formula

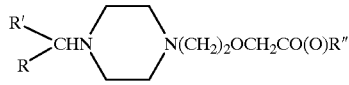

wherein R, R' and R" are as defined above and (b) hydrolyzing said piperazine-substituted aliphatic carboxylate with acid to form said piperazine-substituted aliphatic carboxylic acid.

2. A process for preparing a piperazine-substituted aliphatic carboxylic acid having the formula

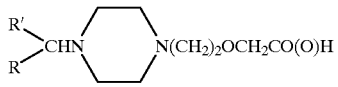

wherein R is phenyl and R' is 4-chlorophenyl, said process comprising (a) treating a solution comprising a compound of the formula

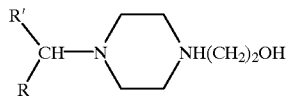

wherein R and R' are as defined above and an aliphatic ester of the formula

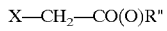

where X is a leaving group and R" is tert-butyl, with a base in the presence of an effective amount of a phase-transfer catalyst selected from the group consisting essentially of tetrabutylammonium bromide, ALIQUAT® 336 Phase Transfer Catalyst, ADOGEN® 464 Phase Transfer Catalyst, TDA-1, tetrabutylammonium hydrogen sulfate, benzyltriethyl-ammonium chloride, cetyltrimethylammonium bromide and tetrabutyl-phosphonium bromide for a time and at a temperature sufficient to form an piperazine-substituted aliphatic carboxylate of the formula

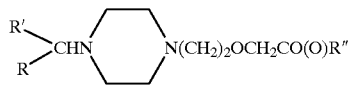

wherein R, R' and R" are as defined above and (b) hydrolyzing said piperazine-substituted aliphatic carboxylate with acid to form said piperazine-substituted aliphatic carboxylic acid.

3. A process for preparing a piperazine-substituted aliphatic carboxylic acid having the formula

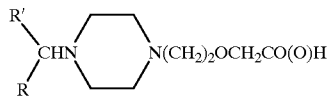

wherein R is phenyl and R' is 4-cholorophenyl, said process comprising (a) reacting a compound of the formula

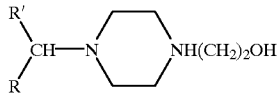

wherein R and R' are as defined above with an aliphatic ester of the formula

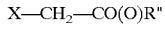

where X is a leaving group and R" is tert-butyl and a base in the presence of an effective amount of a phase-transfer catalyst, for a time and at a temperature sufficient to form a reaction mixture comprising a piperazine-substituted aliphatic carboxylate of the formula

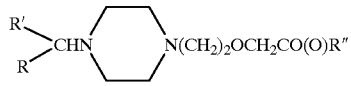

wherein R, R' and R" are as defined above (b) admixing said reaction mixture comprising the piperazine-substituted carboxylate with a liquid, impurity separating agent (c) separating substantially pure piperazine-substituted aliphatic carboxylate from said admixture and (d) hydrolyzing said substantially pure piperazine-substituted aliphatic carboxylate with acid to form said piperazine-substituted aliphatic carboxylic acid.

4. The process according to claim 1 wherein said base is an alkali metal hydroxide.

5. The process according to claim 4 wherein said temperature is from about −10° to about 40° C.

6. The process according to claim 5 wherein said phase-transfer catalyst is a $C_3$ to $C_{12}$ branched alkyl ammonium halide or a $C_1$ to $C_6$ alkyl or aryl phosphonium halide.

7. The process according to claim 2 wherein said temperature is from about −10° to about 40° C.

8. The process according to claim 7 wherein said phase-transfer catalyst is a $C_3$ to $C_{12}$ branched alkyl ammonium halide or a $C_1$ to $C_6$ alkyl or aryl phosphonium halide.

9. The process according to claim 3 wherein said liquid, impurity separating agents is a compound of the formula T—O—T' where T and T' are different and are $C_1$ to $C_6$ linear or branched alkyl.

10. The process according to claim 9 wherein said liquid, impurity separating agent is methyl tertiary butyl ether.

* * * * *